(12) United States Patent
Cowger et al.

(10) Patent No.: US 9,291,552 B2
(45) Date of Patent: Mar. 22, 2016

(54) SYSTEM AND METHOD FOR DETERMINING THE CONCENTRATION OF TETRAHYDROCANNABINOL

(71) Applicant: Engineered Medical Technologies, Meadow Vista, CA (US)

(72) Inventors: Bryan John Cowger, Meadow Vista, CA (US); Megan Anzar Babb, Folsom, CA (US)

(73) Assignee: Engineered Medical Technologies, Sacramento, CA (US)

( * ) Notice: Subject to any disclaimer, the term of this patent is extended or adjusted under 35 U.S.C. 154(b) by 0 days.

(21) Appl. No.: 14/631,995

(22) Filed: Feb. 26, 2015

(65) Prior Publication Data

US 2015/0300947 A1    Oct. 22, 2015

Related U.S. Application Data

(60) Provisional application No. 61/995,805, filed on Apr. 22, 2014, provisional application No. 62/091,952, filed on Dec. 15, 2014.

(51) Int. Cl.
| | |
|---|---|
| G01N 21/00 | (2006.01) |
| G01N 21/33 | (2006.01) |
| G01N 21/03 | (2006.01) |
| G01N 21/13 | (2006.01) |
| G01N 21/17 | (2006.01) |

(52) U.S. Cl.
CPC ............ *G01N 21/33* (2013.01); *G01N 21/03* (2013.01); *G01N 21/13* (2013.01); *G01N 2021/0367* (2013.01); *G01N 2021/1751* (2013.01); *G01N 2201/0446* (2013.01); *G01N 2201/062* (2013.01)

(58) Field of Classification Search
CPC ... G01N 21/534; G01N 21/59; G01N 21/255; G01J 3/42; G01J 1/16
USPC ........................................................ 356/434
See application file for complete search history.

(56) References Cited

U.S. PATENT DOCUMENTS

| | | | | |
|---|---|---|---|---|
| 5,156,952 A | * | 10/1992 | Litman ................ | G01N 33/558 422/412 |
| 2002/0020206 A1 | * | 2/2002 | Mason ............... | G01N 21/8483 73/1.02 |
| 2004/0199059 A1 | * | 10/2004 | Brauker ............. | A61B 5/14532 600/309 |

* cited by examiner

*Primary Examiner* — Tarifur Chowdhury
*Assistant Examiner* — MD Rahman
(74) *Attorney, Agent, or Firm* — Schwabe, Williamson & Wyatt (57) ABSTRACT

The present describes a system and method for determining the concentration of tetrahydrocannabinol (THC) including a tray comprising a first analyte including an infusion of a solvent and cannabis, a light emitting element configured to illuminate the first analyte, a light receiving element configured to receive a first light transmitted through the first analyte, and a control circuit configured to calculate a concentration of tetrahydrocannabinol in the first analyte based at least in part on the first light.

11 Claims, 8 Drawing Sheets

SYSTEM AND METHOD FOR DETERMINING THE CONCENTRATION OF TETRAHYDROCANNABINOL

RELATED APPLICATIONS

The present disclosure claims priority to U.S. provisional application 61/995,805, filed Apr. 22, 2014, and titled "Method of Estimating the Concentration of the Chemical Tetrahydrocannabinol (THC) and Other Active Chemicals in Lipids" and to U.S. provisional application 62/091,952, filed Dec. 15, 2014, and titled "System and Method for Determining the Concentration of Tetrahydrocannabinol," both of which are incorporated herein by reference in their entirety.

TECHNICAL FIELD

The present disclosure relates to a system and method for determining a concentration of tetrahydrocannabinol (THC) in various solvents.

BACKGROUND

Cannabis is a preparation of the cannabis plant often used for its medicinal benefits. The principal psychoactive constituent compound of cannabis is tetrahydrocannabinol (THC), which, when smoked, eaten, ingested, or otherwise consumed, may cause feelings of relaxation and euphoria in some users.

DETAILED DESCRIPTION

Cannabis may be consumed in infusions or solutions in which the cannabis plant is mixed in a solvent and then pressed and filtered to express the oils of the plant into the solvent using the lipophilic properties of the cannabis plant. For example, an infusion of tetrahydrocannabinol (THC) may be accomplished by boiling cannabis plant in water with butter, soaking the cannabis plant in cooking oil, and the like. Examples of solvents include cocoa butter, dairy butter, cooking oil, glycerin, skin lotions, and the like. Depending on the solvent, infusions may be used in the preparation of cannabis edibles like cakes, cookies, brownies, or other cooked or baked items. It is desirable to be able to quantify the concentration of THC and other therapeutic compounds in the infusion so that an appropriate amount of THC can be added during cooking or baking cannabis edibles. Quantifying the concentration of THC in infusions may be accomplished using gas chromatography or mass spectrometry, both of which are expensive and time consuming.

The present disclosure describes a system and method for determining the concentration of THC in an infusion that is inexpensive, quick, and generally accessible outside of a lab environment. An embodiment of the inventive system and method utilizes the high ultraviolet light absorption properties of THC for various wavelengths of light, e.g., ultraviolet (UV) light, to determine the concentration of THC in an analyte. In one embodiment, the system evaluates a first analyte comprising an infusion of a solvent and THC and a second analyte comprising the solvent only by illuminating both with a light emitting element and measuring the intensity of the transmitted light through each using a light receiving element to quantify relative concentrations of THC. The system may make parallel or sequential measurements of both the first and second analytes to improve accuracy. A control circuit quantifies the signal from each, performs the necessary calculations, and displays the result to the user.

Figure 1:
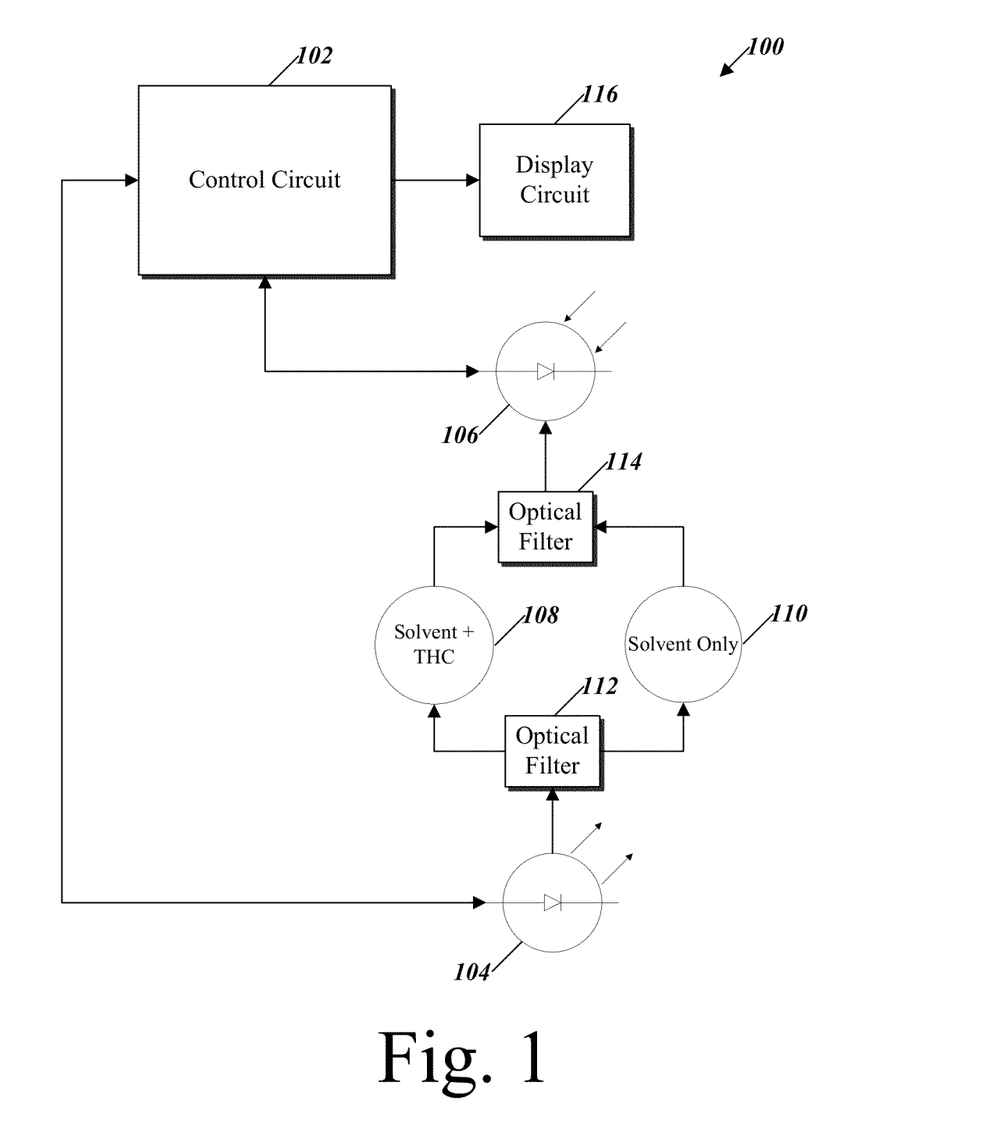
FIG. 1 is a block diagram of an embodiment of a system for measuring the concentration of THC in an infusion according to the present disclosure.

FIG. 1 is a block diagram of an embodiment of a system 100 for measuring the concentration of THC in an infusion according to the present disclosure. Referring to FIG. 1, system 100 comprises a control circuit 102 to control a light emitting element 104 and a light receiving element 106. Control circuit 102 may provide power to the light emitting element 104 and the light receiving element 106 by any means known to a person of ordinary skill in the art, including through the use of batteries. Control circuit 102 may cause light emitting element 104 to emit light of any wavelength, e.g., ultraviolet light. Light emitting element 104 may illuminate a first analyte 108 or a second analyte 110 either substantially simultaneously or sequentially. Light receiving element 106 may convert light transmitted through first analyte 108 or through second analyte 110 into an electronic signal that it provides to control circuit 102.

Light emitting element 104 may be any type of device capable of generating a light known to a person of ordinary skill in the art. Light emitting element 104 may comprise one or more lamps, incandescent bulbs, fluorescent bulbs, solid state light sources, light emitting diodes, and the like. Light emitting element 104 may include one or more light emitting diodes tuned to emit any wavelength of light including ultraviolet light. Similarly, light receiving element 106 may be any type of device capable of receiving light known to a person of ordinary skill in the art. Light receiving element 106 may include one or more photodiodes tuned to receive or sense any wavelength of light including ultraviolet light emitted from light emitting element 104. Light emitting diodes and photodiodes may be advantageously used in system 100 as light emitting element 104 and light receiving element 106, respectively, because they are low in cost and power consumption and high in reliability and space efficiency.

Light emitting element 104 or light receiving element 106 may be a single element or multiple elements depending on the particular implementation of system 100. Light emitting element 104 may be a single light emitting diode, a cluster of single light emitting diodes, or multiple light emitting dies within a single semiconductor package. Similarly, light receiving element 106 may be single photodiode, a cluster of single photodiodes, or multiple photodiodes within a single semiconductor package. Multiple light emitting diodes may yield more optical power and improve reliability at the expense of power consumption and cost increases. Multiple photodiodes may improve sensitivity and reliability at the expense of cost increases. The general operation of light emitting element 104 and light receiving element 106 is well known to a person of ordinary skill in the art and will not be discussed further in any detail.

In an embodiment, light emitted from light emitting element 104 may be filtered before striking first analyte 108 or second analyte 110 using an optional optical filter 112 of any type. Similarly, light transmitted through first analyte 108 or second analyte 110 may be filtered using an optional optical filter 114 of any type.

Light emitting element 104 may be tuned to emit light of different wavelengths. Similarly, light receiving element 106 may be tuned to sense light of different wavelengths. By doing so, light emitting element 104 and light receiving element 106 may be able to extract additional information about first analyte 108 or second analyte 110 beyond a relative measure of THC concentration as we explain in more detail below.

Figure 2A:
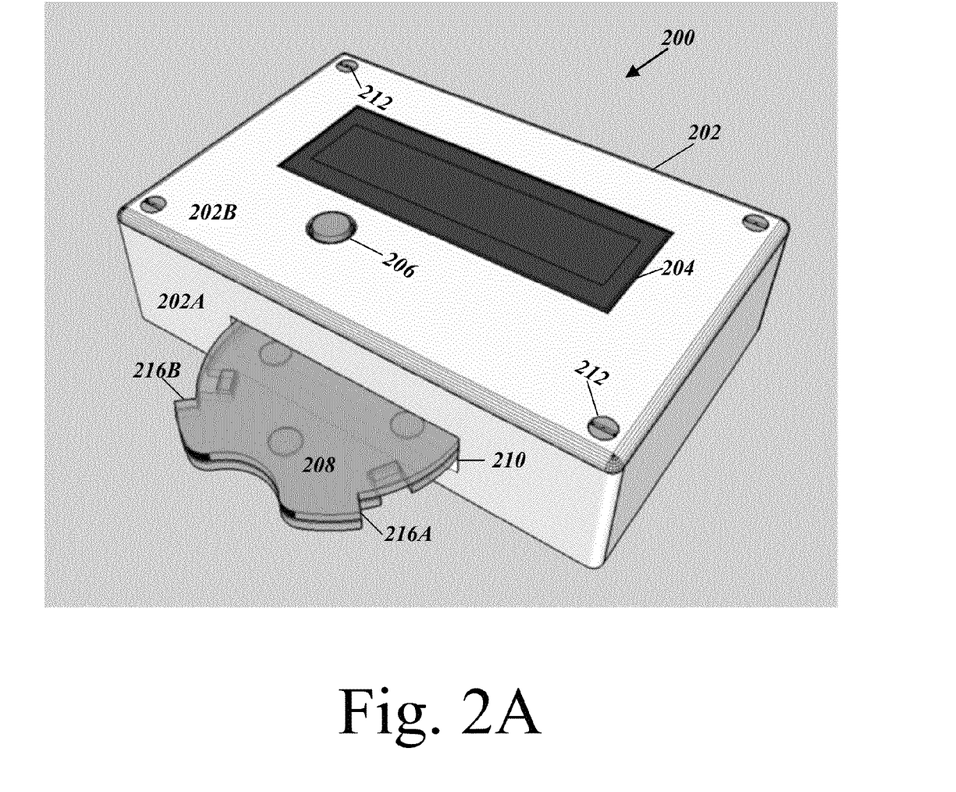
FIGS. 2A-C are different views of an embodiment of a device for measuring the concentration of THC in an infusion according to the present disclosure.

Control circuit 102 may further control display circuit 116 that, in turn, visually displays a concentration of THC to a user using display 204 shown in FIG. 2A.

Figure 2B:
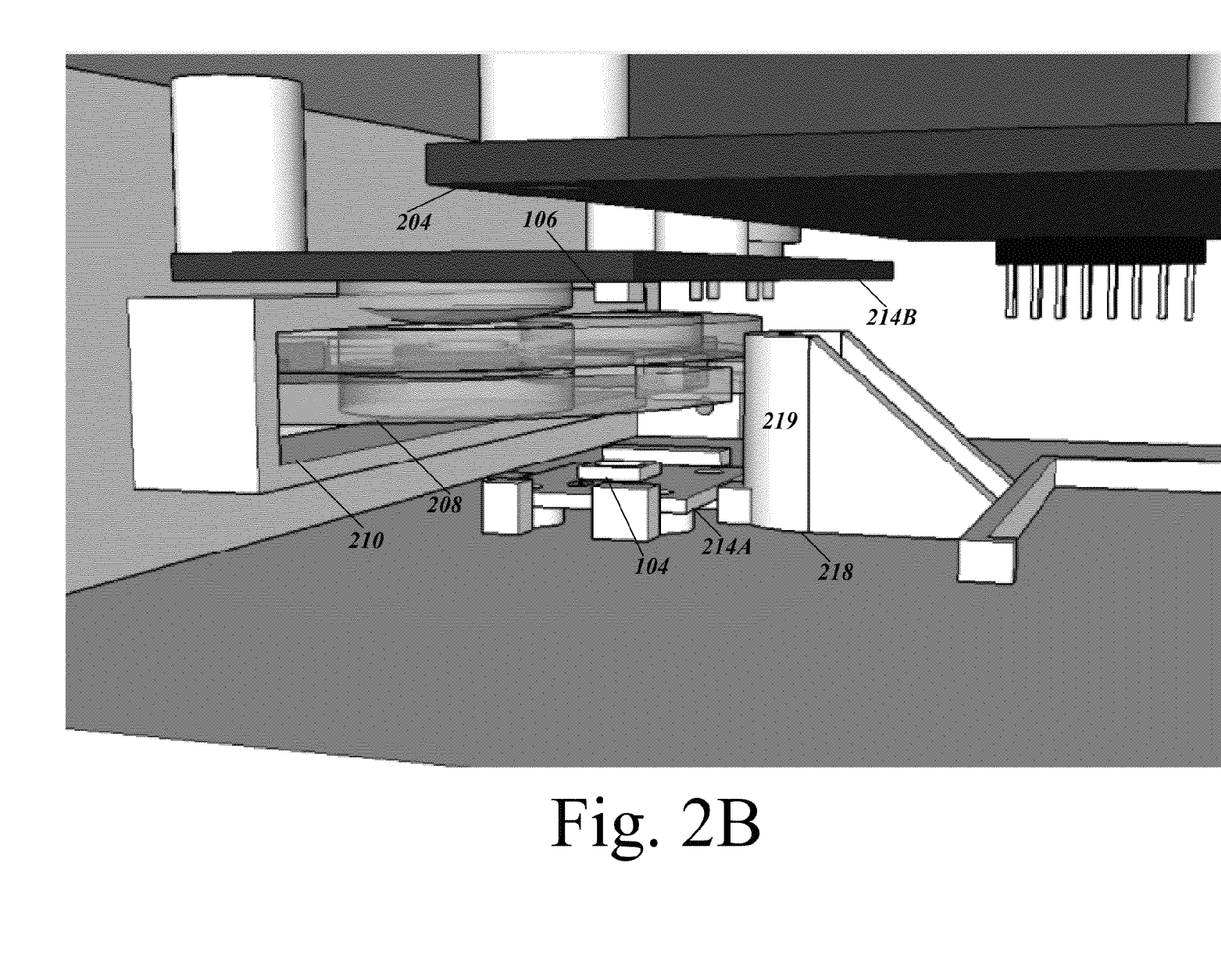
Figure 2C:
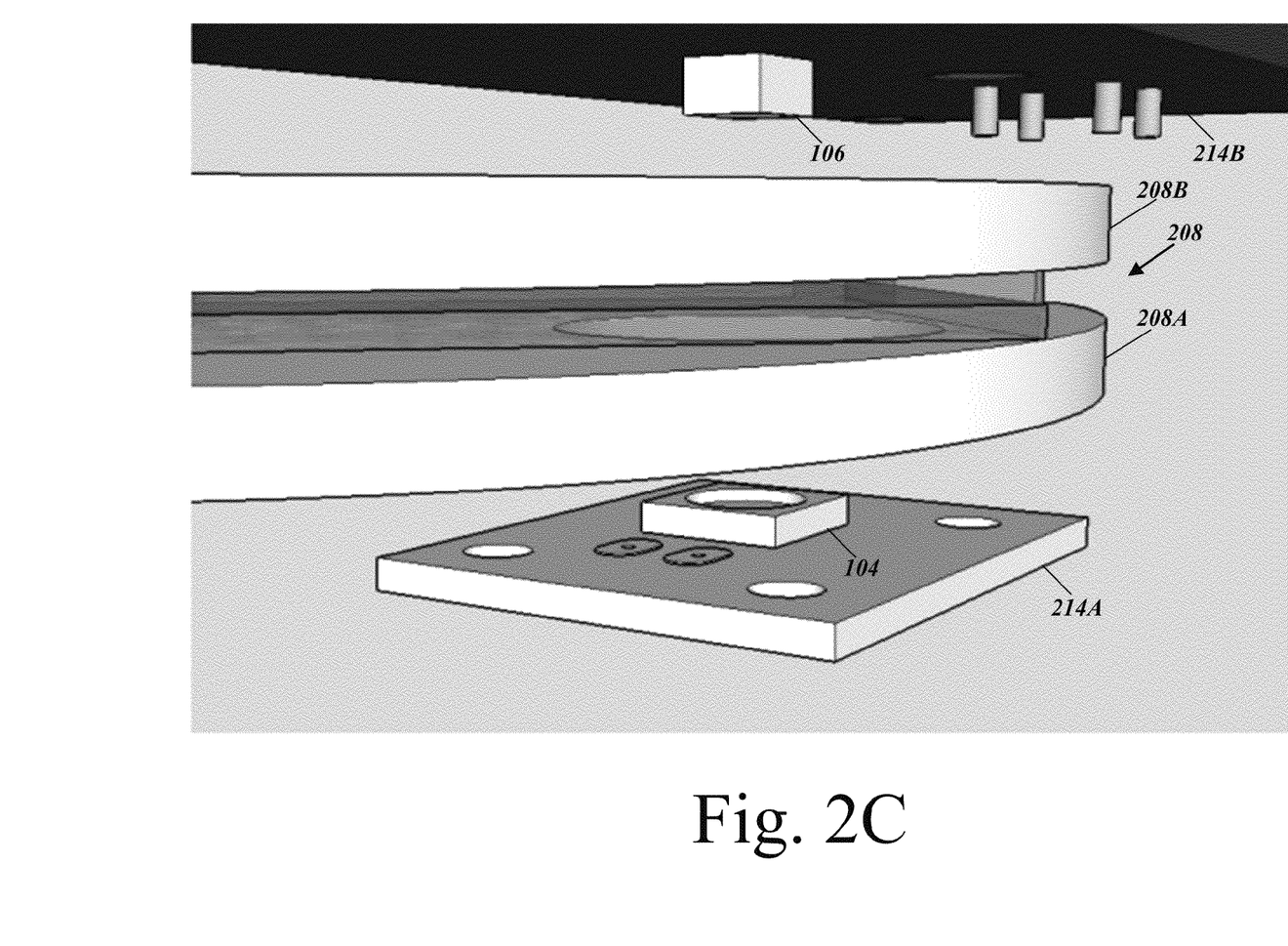

FIGS. 2A-C are different views of an embodiment of a device 200 for measuring the concentration of THC in an infusion according to the present disclosure. Referring to FIGS. 1 and 2A-C, device 200 comprises a housing 202 to house control circuit 102, display circuit 116, display 204, light emitting element 104, light receiving element 106, and optical filters 112 and 114. Housing 202 may receive a tray 208, in turn, containing first analyte 108 and second analyte 110, through a slot 210. Slot 210 may provide mechanical support for tray 208 and may aid in guiding tray 208 into position between light emitting element 104 and light receiving element 106 to facilitate analysis of first analyte 108 or second analyte 110. Alignment post 218 may provide a stop for insertion of tray 208 into housing 202.

Housing 202 may include a switch 206 to power device 200 on or off or to actuate certain menu options displayed on display 204. Switch 206 may operate under the control of circuit 102 and may be any type of switch, actuator, or button known to a person of ordinary skill in the art. Housing 202 may have any shape and size appropriate for its purpose including the rectangular shape shown in FIG. 2A. In an embodiment, housing 202 is sized to be hand-held and easily movable from one location to another. Housing 202 may be made of any material appropriate for its purpose including plastic materials of any type known to a person of ordinary skill in the art. Housing 202 may comprise a bottom portion 202A and a top portion 202B secured together using any type of fasteners 212, e.g., screws, snaps, and the like.

As shown best in FIGS. 2B-C, housing 202 may house control circuit 102 comprising printed circuit assemblies 214A and 214B that may mechanically support and electrically connect the electronic components of control circuit 102 using conductive tracks, pads, and other features etched from copper sheets laminated onto a non-conductive substrate. Printed circuit assemblies 214A and 214B may be single or double sided or multi-layered printed circuit boards. Conductors on different layers may be connected with plated-through holes called vias. Printed circuit assemblies 214A and 214B may include components, e.g., capacitors, resistors, or active devices, that are mounted using through holes or soldered directly onto a surface of printed circuit assemblies 214A or 214B.

Housing 202 may house display circuit 116 and display 204 to provide a user a visual interface to control operation of the device 100 and to display the results of the analysis of first analyte 108 and second analyte 110. Display 204 may be any kind of display, digital or otherwise, segment or two-dimensional, known to a person of ordinary skill in the art.

Housing 202 may house light emitting element 104 vertically optically aligned with light receiving element 106 on either side of tray 208. Light emitting element 104 may be mounted to a printed circuit assembly 214A while light receiving element 106 may be mounted to a printed circuit assembly 214B. Printed circuit assembly 214A may be coupled to printed circuit assembly 214B to allow control circuit 102 to control operation of light emitting element 104 and light receiving element 106. Printed circuit assemblies 214A and 214B may include printed circuit boards made of any material known to a person of ordinary skill in the art. Light emitting element 104 and light receiving element 106 are positioned within housing 202 such that light generated by light emitting element 104 propagates or transmits through first analyte 108 or second analyte 110 on tray 208 to light receiving element 106.

Housing 202 may house one or more batteries (not shown) of any type to provide power to control circuit 102, light emitting element 104, light receiving element 106, display circuit 116, or display 204.

Tray 208 may comprise a bottom section 208A and a top section 208B having a substantially circular outer circumference and may be configured to contain first analyte 108 and second analyte 110. Bottom section 208A may lock to top section 208B using any kind of known locking feature built into or distinct from bottom section 208A or top section 208B. Tray 208 may comprise any material or combination of suitable materials including plastics of any type.

Tray 208 may be received in slot 210 of apparatus 200 to present first analyte 108 or second analyte 110 for analysis. Alignment stop 218 may locate tray 208 in device 200 by preventing tray 208 from being inserted too far into device 200. Stop 218 may have a curved surface 219 to allow for counterclockwise rotation of tray 208 up to rotational end stop 216A or for clockwise rotation of tray 208 up to rotational end stop 216B.

Figure 3A:
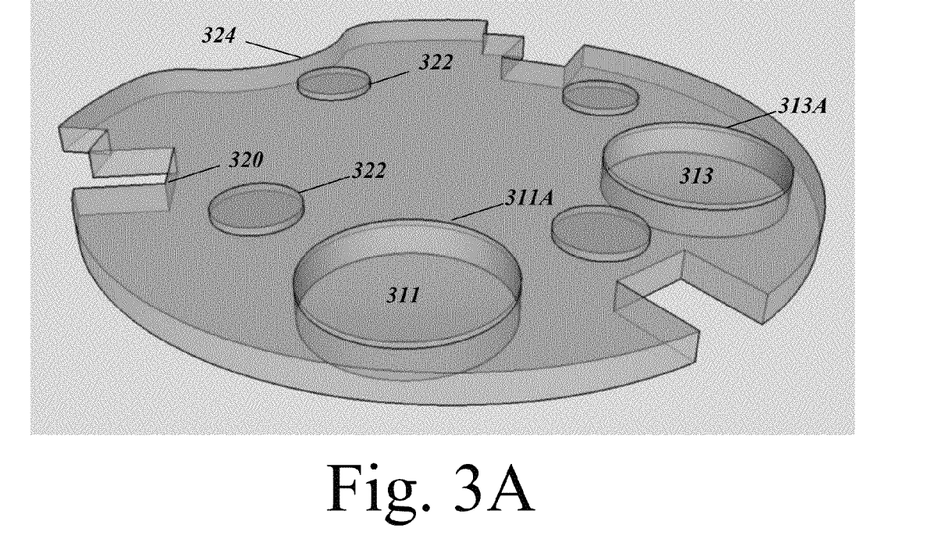
FIGS. 3A-C are different views of an embodiment of a tray for measuring the concentration of THC in an infusion according to the present disclosure.
Figure 3B:
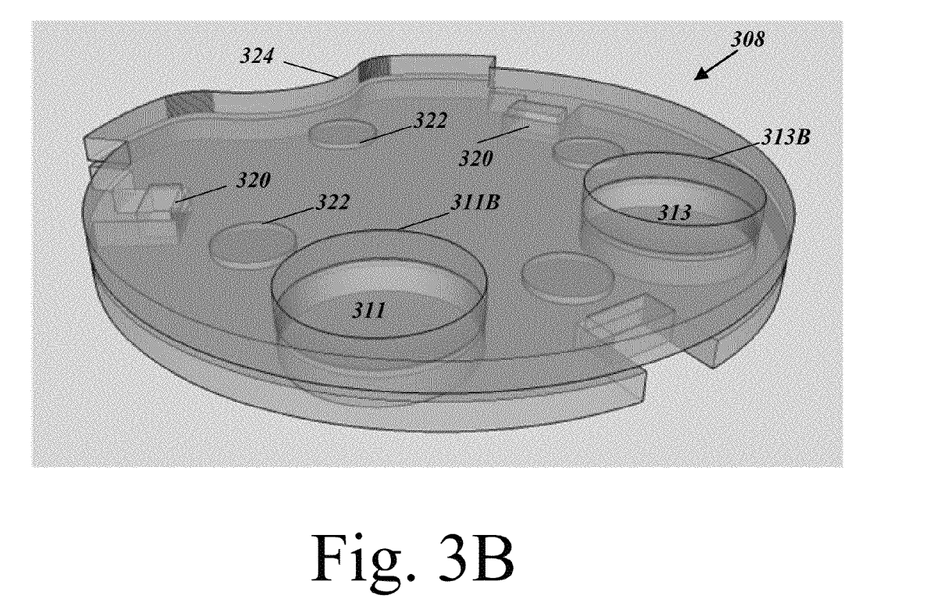
Figure 3C:
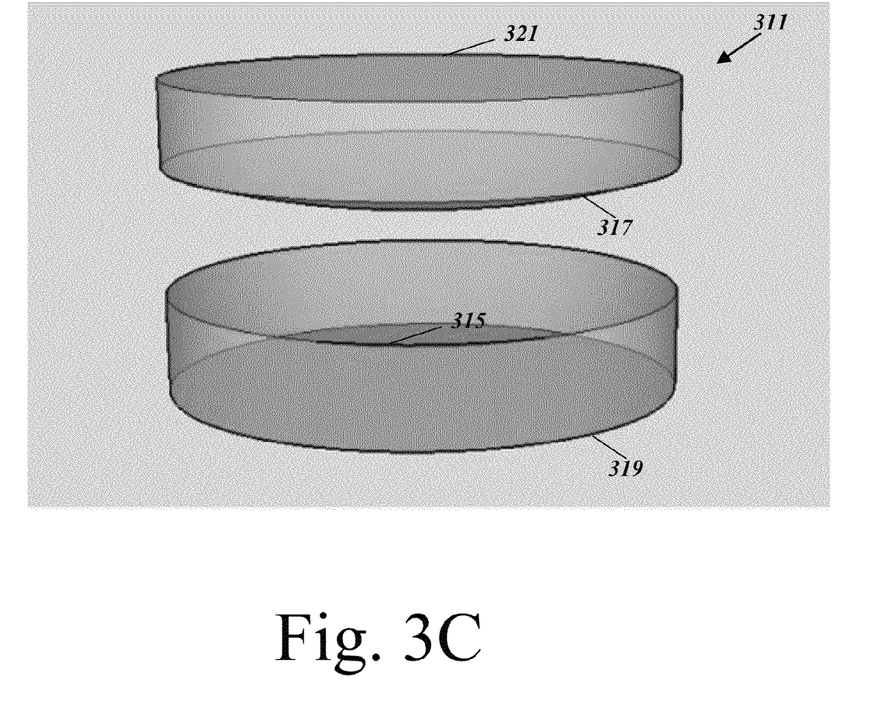

Tray 208 is shown in more detail as tray 308 in FIGS. 3A-C. Referring to FIGS. 2A-C and 3A-C, tray 308 comprises a bottom section 308A and a top section 308B that lock or snap together with locking features 320. Locking features 320 may be latches, snaps, or the like built into bottom section 308A that are received by notches or the like built into top section 308B. Alternatively, locking features 320 may be latches, snaps, or the like built into top section 308B that are received by notches or the like built into bottom section 308A. Locking features 320 may be fasteners distinct from bottom section 308A or top section 308B. Locking features 320 may comprise any material known to a person of ordinary skill in the art including plastics of any type. Locking features 320 may be self-releasing to ensure that bottom section 308A secures to top section 308B (or that top section 308B secures to bottom section 308A) without disturbing first analyte 108 or second analyte 110.

Tray 308 may comprise alignment features 322 built into bottom section 308A that are received by top section 308B that allow for alignment between bottom section 308A and top section 308B in the x, y, and z axis. Conversely, alignment features 322 may be built into top section 308B. Alignment features 322 may have a predetermined height so as to align top section 308A a known vertical distance from bottom section 308B to ensure that first analyte 108 or second analyte 110 has a uniform thickness across a first analyte cavity 311 or a second analyte cavity 313. Alignment features 322 are shown as having a cylindrical shape but other shapes come within the scope of the present disclosure.

Tray 308 may comprise a semicircular thumb well 324 to facilitate insertion of tray 308 into slot 210 of device 200.

Thumb well 324 may facilitate clockwise and counterclockwise rotation of tray 308 about rounded surface 219 of post 218 to present first analyte 108 or second analyte 110 for analysis.

First analyte cavity 311 may comprise a first bottom cavity 311A and a first top cavity 311B. Similarly, second analyte cavity 313 may comprise a second bottom cavity 313A and a second top cavity 313B. First bottom cavity 311A and first top cavity 311B together may contain first analyte 108 (or second analyte 110) when bottom section 308A is secured to top section 308B using locking features 320. Similarly, second bottom cavity 313A and second top cavity 313B may contain second analyte 110 (or first analyte 108) when bottom section 308A is secured to top section 308B using locking features 320.

As best shown in FIG. 3C, first bottom cavity 311A may have a substantially concave surface 315 and first top cavity 311B may have a substantially convex surface 317. When bottom section 308A is secured to top section 308B of tray 308, the convex surface 317 of first top cavity 311B spreads first analyte 108 (or second analyte 110) about the concave surface 315 of first bottom cavity 311A to ensure that first analyte 108 has a uniform thickness throughout first cavity 311. Second bottom cavity 313A and second top cavity 313B may have a construction similar to that shown in FIG. 3C. Note that a height of the alignment features 322 may determine a size of a space between first bottom cavity 311A and first top cavity 311B (or between second bottom cavity 313A and second top cavity 313B) when bottom section 308A is secured to top section 308B to thereby set a thickness of first analyte 108 or second analyte 110 presented for analysis. The meniscus or bowl shape created in analyte cavities 311 and 313 may additionally aid in removal of bubbles within the first analyte 108 or second analyte 110 as the bottom section 308A is secured to the top section 308B. Analyte cavity 311 may be proud relative to immediately surrounding surfaces to allow excess analyte to overflow the edges of first cavity 311 without risk of contaminating an in second cavity 313. Similarly, analyte cavity 313 may be proud relative to immediately surrounding surfaces to allow excess analyte to overflow the edges of second cavity 313 without risk of contaminating an analyte in first cavity 311.

First analyte cavity 311 or second analyte cavity 313 may be made of any material known to a person of ordinary skill in the art including light transmissible (or optically clear) materials such as plastics. First cavity 311 or second cavity 313 may be made of any materials known to a person of ordinary skill in the art including optically clear materials such as plastics. As such, first cavity 311 or second cavity 313 may form part of an optical path between light emitting element 104 and light receiving element 106. First bottom cavity 311A, first top cavity 311B, second bottom cavity 313A, and second top cavity 313B may have a variety of other shapes depending on a variety of design characteristics of tray 308, including characteristics associated with the design of the optical path between light emitting element 104 and light receiving element 106. First bottom cavity 311A may have a concave surface 315 opposing a flat end (as shown in FIG. 3C), a convex end, or a concave end 319 while first top cavity 311B may have a convex surface 317 opposing a flat end (as shown in FIG. 3C), a convex end, or a concave end 321 depending on the performance characteristics of the optical path between light emitting element 104 and light receiving element 106.

First analyte cavity 311 or second analyte cavity 313 may be built into bottom section 308A or top section 308B or be distinct from bottom section 308A or top section 308B, e.g., by using separate glass slides and cover slips to contain first analyte 108 or second analyte 110.

Figure 4:
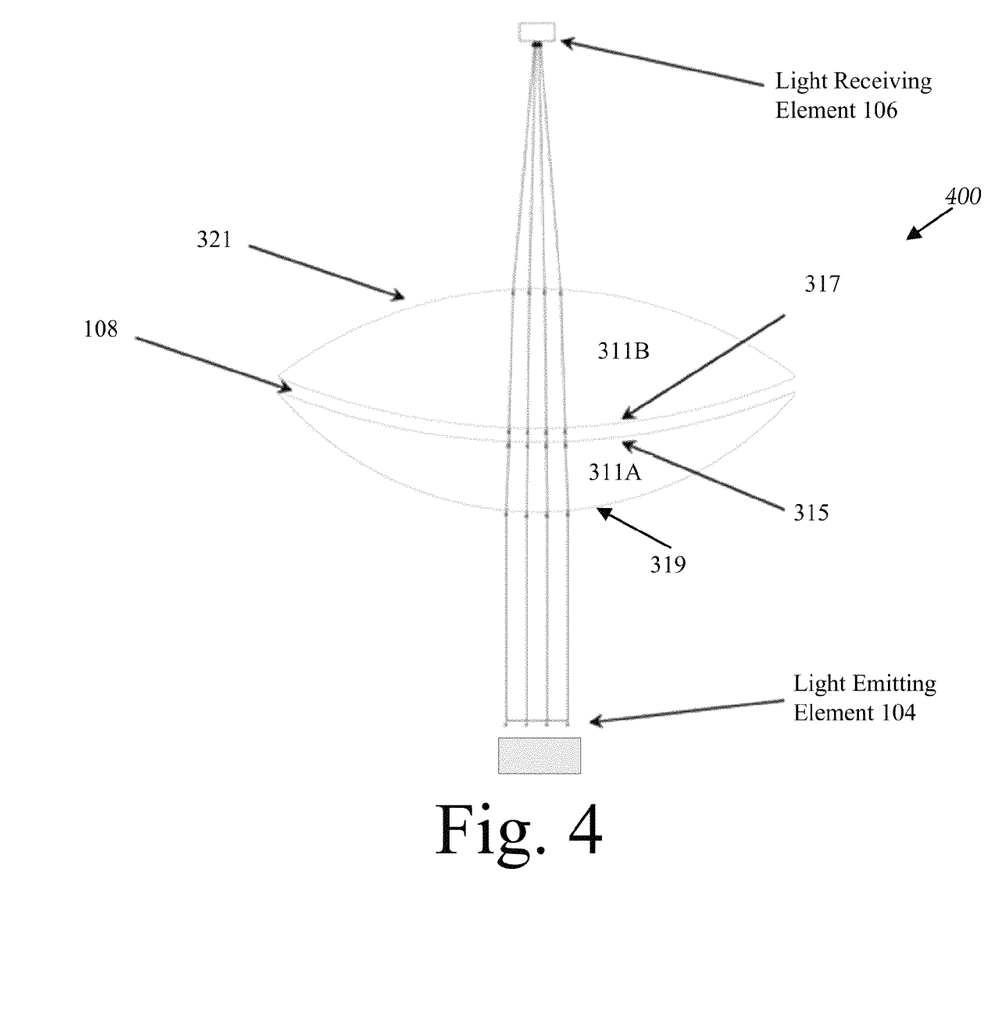
FIG. 4 is a diagram of an embodiment of an optical path for measuring the concentration of THC in an infusion according to the present disclosure.

FIG. 4 is a diagram of an optical path 400 between light emitting element 104 and light receiving element 106 through first analyte 108. Referring to FIGS. 1, 2A-C, 3A-C, and 4, once tray 308 is inserted into device 200, light emitting element 104 generates a light that illuminates cavity 311 containing first analyte 108. First bottom section 311A comprises concave surface 315 and first top section 311B comprises a convex surface 317 that spread analyte 108 uniformly over its length. A convex surface 319 opposes concave surface 315 on first bottom section 311A while convex surface 321 opposes convex surface 317 on bottom section 311B, all of which comprise optically clear materials that may filter the light from light emitting element 108. In an embodiment, the biconvex shape of optically-clear first bottom section 311A secured to first top section 311B may focus the light transmitted through first analyte 108 on to light receiving element 106. A person of ordinary skill in the art should recognize that bottom section 311A and top section 311B may be shaped to variously filter or focus the light emitted from light emitting element 104.

Figure 5:
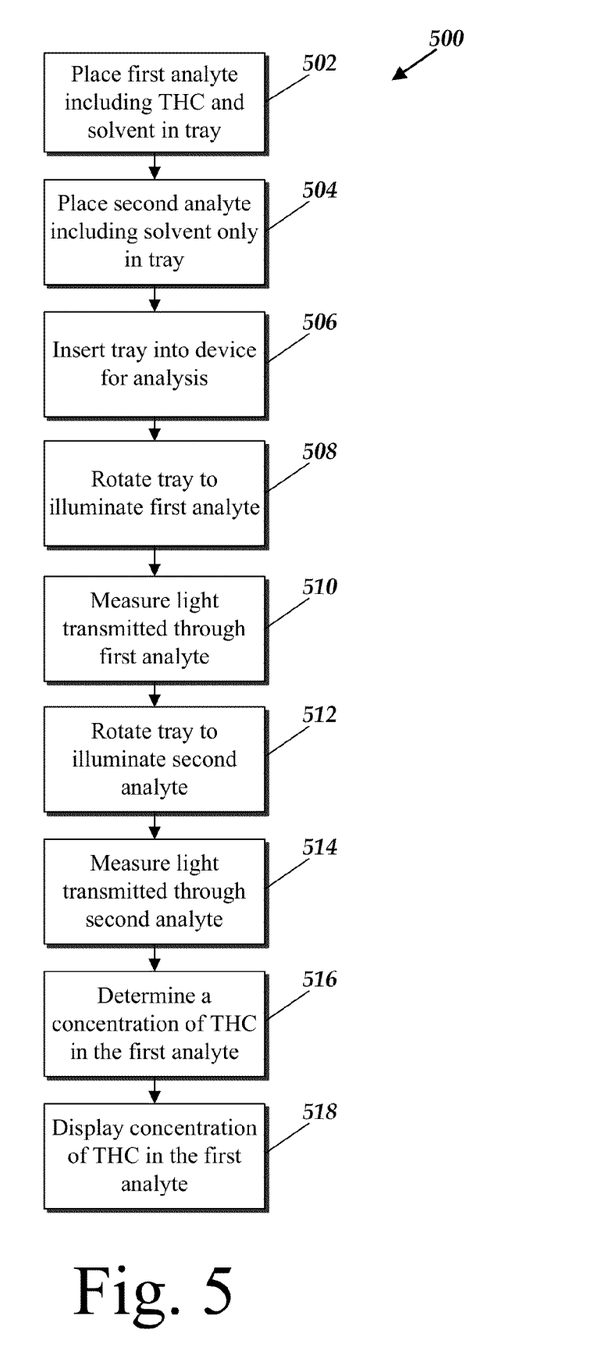
FIG. 5 is a diagram of a method for measuring the concentration of THC in an infusion according to the present disclosure.

FIG. 5 is a diagram of a method 500 for measuring the concentration of THC in a solvent according to the present disclosure. Referring to FIG. 5, at step 502, method 500 includes placing a first analyte including a solvent and THC in a first cavity of a tray and, at step 504, placing a second analyte including the solvent only in a second cavity of the tray. At step, 506, method 500 includes inserting the tray into the device for analysis. At step 508, method 500 includes rotating the tray such that the first analyte is placed in an optical path between a light emitting element and a light receiving element. At step 510, method 500 includes illuminating the first analyte using the light emitting element and measuring the light transmitted through the first analyte using the light receiving element. At step 512, method 500 includes rotating the tray such that the second analyte is placed in the optical path between the light emitting element and the light receiving element. At step 514, method 500 includes illuminating the second analyte using the light emitting element and measuring the light transmitted through the second analyte using the light receiving element. At step 516, method 500 includes determining a concentration of THC in the first analyte by comparing the light transmitted through the first analyte and the light transmitted through the second analyte. At step 518, method 500 includes displaying the concentration of THC. During steps 506, 508, 510, 512, and 514, a same light emitting element and light receiving elements may be used to detect the various positions of the tray.

The invention claimed is:

1. An apparatus, comprising:
    a tray comprising a top portion a top portion and a bottom portion to contain a first analyte in a first cavity and a second analyte in a second cavity, the first analyte comprising a solvent and tetrahydrocannabinol and the second analyte comprising the solvent, the first cavity having a first bottom with a first substantially concave surface and a first top having a first substantially convex surface, the second cavity having a second bottom with a second substantially concave surface and a second top having a second substantially convex surface;
    at least one locking feature to lock the top portion of the tray to the bottom portion of the tray such that the first substantially convex surface substantially uniformly spreads the first analyte about the first substantially concave surface and such that the second substantially convex surface substantially uniformly spreads the second analyte about the second substantially concave surface;

a light emitting device configured to generate a light to illuminate the first analyte and the second analyte contained in the tray with a light;

a light receiving device configured to receive a first portion of the light transmitted through the first analyte and configured to receive a second portion of the light transmitted through the second analyte; and a control circuit configured to determine a concentration of tetrahydrocannabinol in the first analyte based at least in part on a comparison of an intensity of the first portion of the light transmitted through the first analyte received by the light receiving device and the second portion of the light transmitted through the second analyte received by the light receiving device.

2. The apparatus of claim 1, wherein the light emitting device is configured to generate the light to sequentially illuminate the first analyte followed by the second analyte.

3. The apparatus of claim 1, wherein the top portion or the bottom portion comprise at least one horizontal alignment feature, or at least one vertical registration feature.

4. The apparatus of claim 3, wherein the at least one horizontal alignment feature is configured to horizontally align the top portion relative to the bottom portion; and wherein the at least one vertical registration feature is configured to vertically space the top portion from the bottom portion.

5. The apparatus of claim 1, wherein the first cavity or the second cavity comprises an optically clear material having a substantially biconvex outer surface.

6. The apparatus of claim 1, further comprising a display configured to display the concentration of tetrahydrocannabinol in the first analyte.

7. The apparatus of claim 1, wherein the light emitting device comprises at least one light emitting diode; and wherein the light receiving device comprises at least one photodiode.

8. A method, comprising:

containing a first analyte in a first cavity of a tray having a top portion and a bottom portion, the first analyte comprising a solvent and tetrahydrocannabinol and the first cavity comprising a first bottom having a first substantially concave surface and a first top having a first substantially convex surface;

containing a second analyte in a second cavity of the tray, the second analyte comprising the solvent and the second cavity comprising a second bottom having a second substantially concave surface and a second top having a second substantially convex surface;

locking the top portion of the tray to the bottom portion of the tray using at least one locking feature such that the first substantially convex surface substantially uniformly spreads the first analyte about the first substantially concave surface and such that the second substantially convex surface substantially uniformly spreads the second analyte about the second substantially concave surface;

illuminating the first analyte with ultraviolet light;

measuring a first intensity of a first portion of the ultraviolet light transmitted through the first analyte;

illuminating the second analyte with ultraviolet light;

measuring a second intensity of a second portion of the ultraviolet light transmitted through the second analyte; and determining a concentration of tetrahydrocannabinol in the first analyte by comparing the intensity of the first portion of the ultraviolet light transmitted through the first analyte to the intensity of the second portion of the ultraviolet light transmitted through the second analyte.

9. The method of claim 8, further comprising:

sequentially illuminating the first analyte followed by the second analyte with the ultraviolet light.

10. The method of claim 8, further comprising:

illuminating the first analyte in parallel to illuminating the second analyte with the ultraviolet light.

11. The method of claim 8, horizontally aligning the top portion to the bottom portion using at least one horizontal alignment feature; and vertically spacing the top portion from the bottom portion using at least one vertical registration feature.

* * * * *